US012797110B2

(12) United States Patent
Asfora

(10) Patent No.: US 12,797,110 B2
(45) Date of Patent: Nov. 17, 2026

(54) TRANSPARENT SURGICAL EVACUATION PORT DEVICE

(71) Applicant: Asfora IP, LLC, Sioux Falls, SD (US)

(72) Inventor: Wilson Theophilo Asfora, Sioux Falls, SD (US)

(73) Assignee: Asfora IP, LLC, Sioux Falls, SD (US)

( * ) Notice: Subject to any disclaimer, the term of this patent is extended or adjusted under 35 U.S.C. 154(b) by 589 days.

(21) Appl. No.: 18/347,515

(22) Filed: Jul. 5, 2023

(65) Prior Publication Data

US 2025/0009386 A1 Jan. 9, 2025

(51) Int. Cl.
*A61B 17/34* (2006.01)

(52) U.S. Cl.
CPC ...... *A61B 17/3423* (2013.01); *A61B 17/3472* (2013.01); *A61B 2017/3419* (2013.01); *A61B 2017/3437* (2013.01); *A61B 2017/3458* (2013.01); *A61B 2217/005* (2013.01)

(58) Field of Classification Search
CPC ............ A61B 17/3423; A61B 17/3472; A61B 2017/3419; A61B 2017/3437; A61B 2017/3458; A61B 2217/005; A61M 1/64–684; A61M 2039/025
See application file for complete search history.

(56) References Cited

U.S. PATENT DOCUMENTS

| | | | | |
|---|---|---|---|---|
| 6,152,933 | A | 11/2000 | Werp et al. | |
| 7,694,821 | B1 | 4/2010 | Asfora | |
| 8,343,138 | B2 | 1/2013 | Asfora | |
| 2010/0063452 | A1* | 3/2010 | Edelman ............ | A61B 17/3421 604/174 |
| 2011/0160679 | A1 | 6/2011 | Okiyama et al. | |
| 2012/0004629 | A1* | 1/2012 | Asfora .............. | A61M 39/0247 604/319 |
| 2012/0064274 | A1* | 3/2012 | Cai .......................... | C09J 11/06 428/447 |
| 2013/0158578 | A1 | 6/2013 | Ghodke et al. | |
| 2014/0206941 | A1 | 7/2014 | Stiner et al. | |
| 2015/0080708 | A1 | 3/2015 | Piferi | |
| 2017/0291017 | A1 | 10/2017 | Branch, Jr. et al. | |
| 2018/0369556 | A1 | 12/2018 | Anzai | |
| 2022/0249190 | A1* | 8/2022 | Kelly ................. | A61B 17/3417 |

FOREIGN PATENT DOCUMENTS

| | | |
|---|---|---|
| WO | 2016049155 A1 | 3/2016 |

* cited by examiner

*Primary Examiner* — Susan S Su
(74) *Attorney, Agent, or Firm* — Fox Rothschild LLP

(57) ABSTRACT

The present disclosure relates to a surgical evacuation port device, a port body having proximal and distal ends and defining a distal evacuation opening at the distal end, a proximal evacuation opening at the proximal end, and n evacuation lumen extending from the distal to the proximal evacuation opening. At least a viewing portion of the port body that defines the evacuation lumen is made from an optically transparent material that allows a user to optically see into the evacuation lumen to view obstructions therein. The device also includes a bone engagement portion associated with the port body and configured to attach to a bone to enable evacuation of fluid through the evacuation lumen.

22 Claims, 4 Drawing Sheets

TRANSPARENT SURGICAL EVACUATION PORT DEVICE

FIELD OF DISCLOSURE

The present disclosure relates to systems and methods for removing fluids from the subdural region of a patient, and more particularly to a surgical evacuation port device made with an optically transparent material.

BACKGROUND

The subdural space of the human head is the space located between the brain and the lining of the brain, which is referred to as the dura mater (hereinafter referred to as the "dura"). Hemorrhages on the surface of the brain, for example, may cause a condition known as a subdural hematoma. The subdural hemorrhages may have a number of causes. For example, elderly persons may be more susceptible to subdural hemorrhages because as the brain ages it tends to become atrophic and the subdural space between the brain and the dura gradually enlarges. Bridging veins between brain and dura frequently stretch and rupture as a consequence of relatively minor head injuries, thus giving rise to a collection of blood in the subdural space. Further, severe linear acceleration or deceleration of the brain can result in the brain moving excessively with respect to the dura, often causing rupture of the bridging veins or the blood vessels on the surface of the brain, which can in turn cause subdural hemorrhages in an otherwise healthy brain.

These subdural blood collections can be classified as acute subdural hematomas, subacute subdural hematomas, and chronic subdural hematomas. Acute subdural hematomas, which are associated with major cerebral trauma, generally consist primarily of fresh blood. Subacute subdural hematomas are generally associated with less severe injuries than those underlying the acute subdural hematomas. Chronic subdural hematomas are generally associated with even less severe, or relatively minor, injuries. The chronic subdural hematomas tend to be less dense liquid consisting of very diluted blood. Another condition involving a subdural collection of fluid is a hygroma, which is a collection of cerebrospinal fluid (sometimes mixed with blood) beneath the dura, which may be encapsulated.

Devices such as subdural evacuation port devices are generally known and are capable of draining fluid from the subdural region. However, such known devices are made from opaque materials, such as surgical steel which are not optically transparent. As such, when a blockage occurs (e.g., a blood clot) within the device or proximate its distal opening, a user is unable to determine the cause and location of the blockage, and cannot take appropriate corrective action.

The current disclosure describes systems and methods for addressing at least some of the issues discussed above.

SUMMARY

The present disclosure relates to systems, methods and devices for draining fluid using a surgical evacuation port device made from an optically transparent material.

In some aspects, the disclosure relates to a surgical evacuation port device, that may include a port body having proximal and distal ends. The body may also include a distal evacuation opening at the distal end, a proximal evacuation opening at the proximal end, and an evacuation lumen extending from the distal to the proximal evacuation opening. A least a portion of the port body includes a viewing portion that defines the evacuation lumen and is made from an optically transparent material that allows a user to optically see into the evacuation lumen to view obstructions therein. The device additionally includes a bone engagement portion associated with the port body and configured to attach to a bone to enable evacuation of fluid through the evacuation lumen.

In various embodiments, the viewing portion may be a window, and a remainder of the body around the window may be optionally less transparent or opaque. Optionally, the viewing portion may surround the evacuation lumen. In some embodiments, the entire port body may be formed from the optically transparent material. In various other embodiments, the entire surgical evacuation port device may be formed from the optically transparent material.

In some other embodiments, the proximal end may include a fitting configured to operably connect to a suction device.

In various embodiments, the bone engagement portion may be configured to mount the port body through a hole in the bone to evacuate fluid through the evacuation lumen across the bone. In some other embodiments, the bone engagement portion may include threads disposed about the exterior of the distal end of the body and configured to screw into bone. In some embodiments, the threads may be configured and dimensioned to screw into a skull to position the body in communication with the subdural region of the cranium. In some embodiments, at least a portion of the bone engagement portion may be optically transparent to allow the user to optically see into the evacuation lumen.

In another embodiment, the device may include a needle access port defining an access port lumen in communication with the evacuation lumen to perform an operation at a sight of a blockage therein, and a seal that may seal the needle access port to preserve a suction within the evacuation lumen. In some embodiments, the needle access port may include an access port viewing portion formed from an optically transparent material to allow a user to see therein.

In yet another embodiment, the viewing portion may be made from an optically transparent polymer. Optionally, the optically transparent polymer may be polycarbonate. Optionally, the optically transparent polymer may be crystalized acrylonitrile butadiene styrene (ABS).

In another aspect, the present disclosure relates to a surgical evacuation port device configured for removal of fluid from a subdural space. The surgical evacuation device includes a port body having proximal and distal ends. The body includes a distal evacuation opening at the distal end, a proximal evacuation opening at the proximal end, and an evacuation lumen extending from the distal to the proximal evacuation opening. The port body includes at least a viewing portion that defines the evacuation lumen and is made from an optically transparent material that allows a user to optically see into the evacuation lumen to view obstructions therein. The device additionally includes a bone engagement portion associated with the port body and including threads that are configured and dimensioned to screw into a skull to position the body in communication with the subdural region of the cranium and a fitting associated with the port body configured to attach to a suction device to provide suction to the subdural region of the cranium.

In some embodiments, the viewing portion may be a window, and a remainder of the body may be less transparent or opaque. In some other embodiments, the viewing portion may surround evacuation lumen. In yet another embodiment, the entire body may be formed from the optically transparent material.

In some examples, the surgical evacuation port device may include a needle access port defining an access port lumen in communication with the evacuation lumen to perform an operation at a sight of a blockage therein, and a seal that seals the needle access port to preserve suction within the evacuation lumen. In some embodiments, the needle access port may include an access port viewing portion formed from an optically transparent material to allow a user to see therein.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION

As discussed above, devices for clearing the subdural space of the human brain are known (for example, see U.S. Pat. No. 7,694,821). The systems of the prior art generally includes a subdural evacuation port device, and devices for evacuating a collection of fluid from a subdural space of a patient that incorporate the subdural evacuation port device. However, such devices and systems are made of opaque materials such as surgical steel. Often, blockages due to blood clotting or other issues may occur within these devices (and/or in proximity of the opening within the subdural space), and opaque material prevents a user from optically determining the cause and/or location of the blockage. As such, the user is unable to determine appropriate blockage removal protocols or steps without the use of special non-optical imaging techniques and/or removal of the evacuation port device itself.

Figure 1:
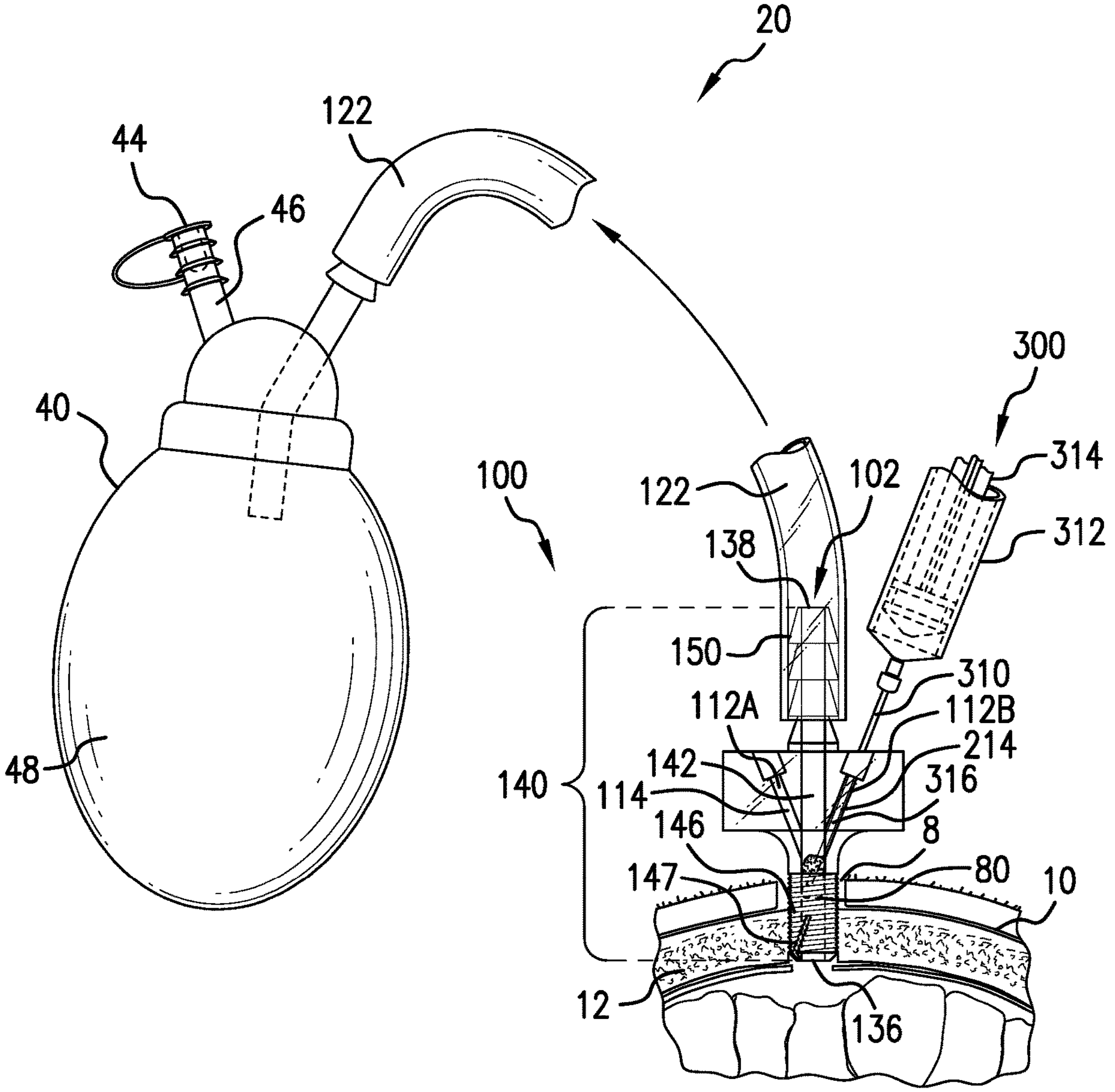
FIG. 1 is a surgical evacuation system in accordance with the principles of the present disclosure.

Referring to FIG. 1, a system 20 in accordance with the principles of the present disclosure is shown. The system includes a surgical evacuation port device 100 and a suction device 40 that is configured to provide a suction (e.g., a negative pressure, a partial vacuum, aspiration, or any other force that can cause aspiration of the fluid without causing damage to and/or suction of tissue in and around the surgical tissue). In some examples, the system 20 additionally includes a needle system 300 configured to assist with removal of blockages.

The system 20 is depicted having the surgical evacuation port device mounted at a hole 8 in a skull 12 (also known as a trephination) of a patient. In embodiments where fluid is drained through a hole, such as the hole 8, a drill device can be provided for drilling the hole into the bone of a patient after an incision has been made in a scalp (e.g., subcutaneous tissue, the galea, and the periosteum) of the patient. A drill bit is mountable on the drill device in a suitable manner, such as by an adjustable chuck assembly, internally within the drill body or any other suitable means. The drill bit can be rotated by manual means (e.g., turned by the surgeon's hand), by motorized means, or any other suitable means. Preferably, the drill device includes a drill stop for selectively limiting the maximum penetration of a tip of the drill into the skull of the patient. The drill device can additionally be used in embodiments of the present disclosure. In embodiments where the surgical evacuation port device 100 is used to drain fluid adjacent to a bone, a drill is not typically used, and an incision is made through skin of the patient. It will be appreciated that the device can be configured to engage with any bone other than the skull such as, without limitation, spine, hip, etc. The system 20 can additionally be configured to drain fluid near or adjacent to any other bone.

As shown in FIG. 1, the suction device 40 is attached to the surgical evacuation port device 100 and configured to create a suction (uniform or non-uniform) through an evacuation lumen 142 of the surgical evacuation port device 100 and in a surgical area from which fluid needs to be evacuated (e.g., a subdural space) of the patient to allow built up fluid to be evacuated from the subdural space through the hole 8. However, the disclosure is not so limiting, and in various examples, the system 20 can be used to evacuate fluid adjacent a bone, within a different bone or any other suitable area that requires draining, fluid aspiration, and/or suction therethrough. In some embodiments, the suction device 40 is attached to a conduit 122 which in turn is attached to a fitting 150 on the subdural evacuation port device 100, in order to provide a uniform suction through the evacuation lumen 142 of the surgical evacuation port device 100. The fitting 150 surrounds a proximal end 138 of the port body 140 of the surgical evacuation port device 100 such that the conduit can be attached at the primary evacuation opening (the fitting 150 is discussed in greater detail below).

The suction device 40 exerts a suction pressure (e.g., a negative pressure) for imparting a uniform partial vacuum (or suction) in the evacuation lumen of the surgical evacuation port device. In some embodiments, the suction device is a manual device such as a Jackson-Pratt bulb, or other suitable pump. In other embodiments, the suction device is electronic or powered. The magnitude of the suction created is relatively low for exerting a gentle aspiration or suction in the subdural space, when the device is used to drain the subdural region. The substantial uniformity of the suction pressure is considered important for promoting the gradual re-expansion of the brain in the subdural space.

As depicted, the suction device 40 is a manual suction device and includes a bulb pump. In certain embodiments, a conduit 122 (e.g., a hollow tube or pipe) can connect the fitting 150 and the suction device 40 with one another. In certain embodiments, the suction device 40 includes a vent 46 for allowing air to escape. In certain examples, the vent 46 is a one-way valve for expelling air from the bulb pump 40 when it is pumped and gently suctioning through the conduit 122 when air returns to the suction device. In some other embodiments, the conduit 122 or the suction device 40 can include a check valve. The suction device 40 can additionally include a plug 44 which can be inserted into vent 46 to prevent fluid from escaping the suction device 40. In certain examples, squeezing of suction device 40 can create a partial vacuum through the evacuation lumen and gently suction out or aspirate any fluid from the space from which fluid needs to be aspirated (e.g., a bone and surrounding area) into evacuation lumen 142 and subsequently into the conduit 122. The conduit 122 can be formed from a material that is sufficiently rigid to not collapse under the suction applied by suction device 40. In certain embodiments, the conduit can be formed from a transparent material. In some examples, the suction device 40 includes a reservoir 48 to contain or hold fluid suctioned by the surgical evacuation port device. In certain embodiments, the reservoir has a volume about 100 ml, about 125 ml, about 150 ml, about 175 ml or any other suitable. In some other examples, the reservoir 205 has a volume of about 100 ml-175 ml, about 120 ml-160 ml, 130 ml-150 ml, 135 ml-145 ml or any other suitable range of volumes.

In various embodiments, the magnitude of the suction pressure exerted by a typical evacuation device is about 0.8 inch to 1 inch of mercury (Hg) with respect to atmospheric pressure. Depending on the procedure, it will be appreciated that a lower level (e.g., less than 0.8 inches of mercury) of suction pressure may be used. While relatively higher levels of suction pressure may be used (such as up to approximately 1.2 inches of mercury), significantly higher levels of suction pressure can damage brain tissue and/or hamper the recovery of the brain and the associated tissues, by, for example, causing hemorrhages to occur. As such, an optimal suction pressure may be used that permits the suction pressure condition to be maintained in the subdural space of the patient for a relatively extended period of time for removing any further collection of fluid, as well as promoting a gradual expansion of the brain in the subdural space during the healing process. The components used to construct subdural evacuation port device are sufficiently strong to sustain a suction of this level without collapsing (discussed in further detail below). As discussed above, it will be appreciated that any suitable evacuation device providing such pressure can be configured to attach to the primary evacuation portion 105. In some examples, the negative pressure is about 0.5 in of Hg about 0.6 in of Hg, about 0.7 in of Hg. 0.8 in/Hg, about 0.9 in of Hg, about 1 in of Hg, or any other suitable negative pressure. In some embodiments, the negative pressure is between about 0.5 in of Hg-1 in of Hg, about 0.55 in of Hg-0.95 in of Hg, about 0.7 in of Hg-0.9 in of Hg, about 0.75 in of Hg-0.85 in of Hg or any other suitable ranges of pressure.

The surgical evacuation port device 100 includes a port body 140 having a distal end 136 and a proximal end 138. The distal end 136 includes a distal evacuation opening 104 and the proximal end 138 includes a proximal evacuation opening 102. An evacuation lumen 142 extends through the port body 140 of surgical suction device 100 between the distal evacuation opening and the proximal evacuation opening. The port body 140 includes an optically transparent viewing portion (discussed below in more detail) that is configured to allow a user to optically see the evacuation lumen 142 and view obstructions (and/or other components such as a needle) contained therein. The viewing portions may allow a user to optically see within other portions of the surgical evacuation as discussed below. The surgical evacuation port device additionally includes a bone engagement portion 146 that is configured to attach to bone of a patient such as the skull (discussed in further detail below).

As discussed above, a blockage (e.g., due to a blood clot, thrombus, tissue debris, etc.) may occur in the evacuation lumen and/or an area surrounding the distal opening of the evacuation lumen that can prevent or slow down the suction of fluid from the surgical site of interest. Furthermore, the blockage can cause creation of high or uneven pressure within the evacuation port device and/or the surgical site potentially causing or increasing the risk of tissue damage and hampering tissue recovery at the surgical site. An example blockage 80 is shown in the evacuation lumen 142 of the surgical evacuation port device. Often when the occurrence of a blockage is not detected and/or its cause or location is not timely or accurately determined, a user may increase the suction pressure through the evacuation lumen when suctioning of the fluid stops or slows down. While this can cause removal of the blockage, the increased suction pressure can cause damage to the brain once the blockage is removed (particularly if the suction pressure is not immediately lowered following removal of the blockage). In the prior art subdural evacuation port devices discussed above (e.g., the device of U.S. Pat. No. 7,694,821) where the device is made from opaque material the occurrence of blockages may not be detected leading to the user using increased suction pressure. The presence of a blockage that is not detected can also cause other unintended consequences. For example, the user may stop suction of fluid prior to all of the fluid in the subdural area being drained when the fluid suction stops and/or slows assuming all fluid is withdrawn; apply excessive suction pressure to the brain of the patient; apply a non-uniform suction through the evacuation lumen; and/or other issues. As such, if a blockage 80 occurs during aspiration of fluid from the surgical site of interest, it is desired to dissolve, reposition, and/or remove the blockage As discussed above, currently known evacuation devices are made from utilize opaque materials such as surgical steel, opaque polymers, and other opaque materials. As such, special non-optical imaging methods such as ultrasound, magnetic resonance imaging (MRI), computerized tomography (CT) scans or other suitable imaging technology is required to see within the evacuation lumen of such devices. The present disclosure relates to a surgical evacuation port device that allows for a user or medical professional to optically detect and/or assess the location, type, size, or other properties of a blockage formed within the evacuation lumen (and/or the surgical site proximate the evacuation lumen) without removal of the surgical evacuation port device from the surgical site and/or without stopping the suctioning operation of the surgical evacuation port device (and, optionally, without the use of non-optical imaging technology). The present disclosure additionally the user to determine the methods for removal of the detected blockage (e.g., based on the location and properties such as size, density, etc.) as well as monitor effectiveness of a method for removal of the blockage (and adjust it for optimal removal).

The systems and methods of the current disclosure can be used in association with those described in co-pending U.S. patent application Ser. No. 18/347,474, filed on Jul. 5, 2023 and having a title "SUBDURAL EVACUATION PORT WITH NEEDLE ACCESS PORT", the disclosure of which is incorporated by reference herein in its entirety. The aforementioned co-pending application describes subdural evacuation port devices that include needle access ports for introducing tools into the device primary lumen where the tool (e.g., a needle) can perform an operation to assist in removal of the blockage. Examples of the operation can include, without limitation, delivery of various materials (e.g., thrombolytic agents) to dissolve or reduce the size of blockages, repositioning of the blockage, breaking up the blockage and/or suction or aspiration of the blockages through the tools. Needle access ports include an access port lumen in fluid communication with the evacuation lumen.

The access port lumen and needle access ports are disposed and oriented within the subdural evacuation port and with respect to each other so as to allow a tool (e.g., a needle) to be inserted into the access port lumen and extend into the evacuation lumen and perform an operation to assist in removal of the blockage. For example, the needle can be used to withdraw a blockage from the evacuation lumen through the needle. Alternatively, needles can be used to deliver various agents (e.g., thrombolytic agents) at or near the blockage to dissolve or partially dissolve the blockage. For example, thrombolytics are medications used to dissolve blood clots, specifically thrombi by activating the fibrinolytic system. Some examples of thrombolytics that can be used include, but are not limited to: Alteplase, Reteplase, Tenecteplase, streptokinase or any other suitable, tissue plasminogen activator (tPA), streptokinase (SK), and urokinase (UK), or any other suitable thrombolytic agent. In other examples, a use can break up and/or reposition the blockage using other mechanisms.

Referring again to FIG. 1 and FIG. 2 the system and the surgical evacuation port device are now discussed in greater detail. The port body 140 includes the evacuation lumen 142 that extends through the port body 140 from the distal to proximal end 138, 136 and defines a primary evacuation opening 102 at the proximal end 138 and a distal opening 104 at the distal end 136. The port body 140 can additionally be any other suitable shape such as oval, rectangular or any other suitable shape.

The surgical evacuation port device 100 is connected to the conduit 122 at a fitting 150. The fitting 150 is depicted as a barb type fitting, however, the fitting can be any interface that connects the evacuation lumen 142 to the conduit 122 in an air-tight manner, including but not limited to threaded fitting, a snap-fitting, or any other suitable fitting. The conduit 122 is attached, as discussed above, to the suction device 40. In alternative embodiments, the suction device 40 can be directly attached to the proximal evacuation opening 102.

Figure 2:
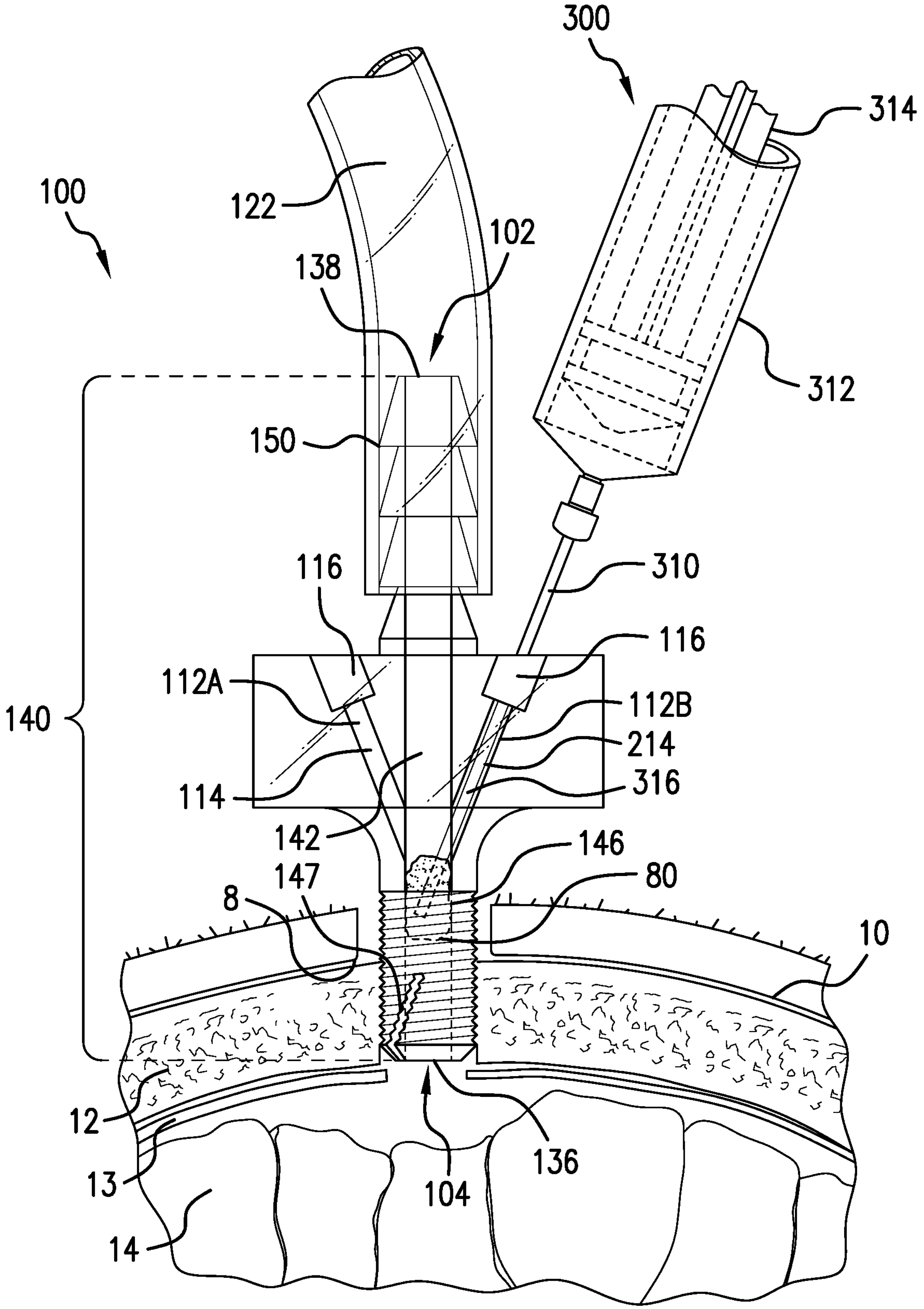
FIG. 2 is a side view of an embodiment of a transparent surgical evacuation port device having needle access ports and mounted within a skull of a patient, in accordance with the present disclosure.

The surgical evacuation port device 100 includes a bone engagement portion 146. The bone engagement portion is configured to mount the port body through a hole in a bone to aspirate fluid from the bone and/or surrounding areas thereof through the evacuation lumen when a suction pressure is applied. The bone engagement portion can additionally be configured to mount the port body near any area that requires drainage of fluid therefrom. FIGS. 1 and 2 illustrate the bone engagement portion being disposed around the distal end of the device. The bone engagement portion 146 can, however, be positioned at any other suitable location allowing for engagement of the port body with the bone. For example, the bone engagement portion 146 could be positioned near the center of body 140 and extend downwardly as a flange with screws or be configured at any other suitable location to allow the device to engage with the skull.

As shown in the figures, the bone engagement portion 146 includes threads that include a flute 147 and is self-tapping. The bone engagement portion 146 can include any other type of threads. Optionally, any other engagement mechanisms allowing for engagement with a bone (e.g., skull) are additionally possible such as, without limitation, friction fit, drilling, tapping, a flange having screws disposed thereon or any other suitable engagement mechanism.

In some embodiments, the bone engagement portion is a skull engagement portion and configured to be sized to fit within a hole in the skull. In some embodiments, the skull engagement portion includes threads that have a diameter of 4.5 mm, 5 mm, about 5.5 mm, about 6 mm about 7 mm, 7.5 mm, about 8, or any other suitable diameter. In some embodiments, the threads have a diameter between about 7-8 mm, about 7.2-7.8 mm, about 7.4-7.6 mm, 4-6 mm about 4.5 mm-5.5 mm, about 4.7-5.2 mm, or any other suitable range of diameters. In some other embodiments, the threads are configured as straight threads. In some other embodiments, the threads are trapezoidal threads. In some embodiments, the threads are pipe threads. In some examples, the threads are coarse and have a pitch of about 1 mm, about 1.5 mm, about 2 mm, about 2.5 mm or any other suitable pitch. In some examples, the threads have a pitch between about 1 mm-2.5 mm, about 1.2 mm-2.2 mm, about 1.4 mm-2 mm or any other suitable range.

In various embodiments, the surgical evacuation port device of FIGS. 1 and 2 includes needle access ports 112A, 112B. The needle access ports 112A, 112B include access port lumens 214 that are in fluid communication with the evacuation lumen 142. The access port lumens 214 are disposed and oriented with respect to the port body 140 to allow a needle inserted into the access port lumen 214 to extend into the evacuation lumen. As depicted, there are two needle access ports 112A, 112B disposed on opposite sides of the port body 140. In some examples, the needle access ports 112A, 112B can be configured as protrusions that extend away from the port body 140. The protrusions (not shown but discussed in the above referenced co-pending U.S. patent application Ser. No. 18/347,474) can be rigid, semi-rigid, or non-rigid protrusions. It will be appreciated that the surgical evacuation port device 100 can also include more or less needle access ports that can be disposed at any location on the port body 140 allowing a tool to access the evacuation lumen 142. For example, the surgical access port 100 can include one needle access port, three needle access ports or any other suitable number of needle access ports. The needle access ports 112A, 112B can also include seals 116 that are configured to maintain suction within the evacuation lumen 142 when a needle is inserted into the needle access ports 112A, 112B. The seals 116 are depicted as plugs that are disposed at the proximal end of the needle access ports 112A, 112B (i.e., the ends that are one the opposite side with respect to the evacuation lumen 142). It will be appreciated that the seals can be located at any location in the needle access port and can be formed of any suitable material (e.g., self-sealing materials). In various embodiments, other examples of seals include but are not limited to caps, silicon, rubber, natural rubber or any other suitable material or type of seal.

As depicted in FIGS. 1 and 2, a needle system 300 may be configured to be coupled with the needle access ports 112A and 112B. The needle system may include a needle 310 that extends into the needle access port 112B. The needle 310 is configured to perform an operation to assist with removal of the blockage 80 as depicted within the evacuation lumen 142.

It will be appreciated that any other tool such as a suction device, syringe or any other suitable device can also be used to access the needle access ports 112A, 112B to remove and/or assist with removal of the blockage 80. The needle 310 includes a needle body that is hollow and has a needle lumen 316. In some embodiments, the needle is a lumbar puncture needle and can include a stylet (not pictured) that is inserted through the needle lumen 316 to puncture the seal. After the seal 116 is punctured and the needle body extends through the seal, the stylet can be withdrawn from the needle lumen 316. It will be appreciated that any other suitable needle is additionally possible. For example, a blunt needle, a rigid needle, a non-rigid needle or any other suitable tool. Additionally, any other suitable device can be used to puncture the seals 116. The needle system 300 may include a withdrawal mechanism 312 coupled to the needle 310. As depicted, the withdrawal mechanism 312 is a syringe having a plunger 314.

In some embodiments, withdrawal mechanism 312 can be any device that provides a suction through the needle lumen 316 for withdrawal or breakage of the blockage (or pieces/debris thereof). For example, the withdrawal mechanism can be an electronic device that provides suction through the needle lumen 316. As depicted, plunger 314 can be used to provide a suction force through the needle lumen 316 to suction or break up the blockage 80. For example, the plunger may be withdrawn proximally towards a user to create the suction force.

Additionally, and/or alternatively, withdrawal mechanism 312 can be any device that provides delivery of an agent at or near the blockage. For example, the syringe 312 can be filled with a thrombolytic agent which can be introduced to the blockage by depressing the plunger 314 in the distal direction for delivering the thrombolytic agent from the syringe body at, near, or into the blockage 80. The thrombolytic agent may at least partially dissolve the blockage. The syringe may then, optionally, be used to suction the debris of the thrombolized blockage and/or any non-thrombolized portions of the blockage by, for example, withdrawing, the plunger proximally towards a user to create the suction force. Optionally, the debris of the thrombolized blockage and/or any non-thrombolized portions of the blockage may be aspirated via the evacuation lumen along with the fluid being evacuated. In some embodiments, the needle 310 is configured to extend into the blockage 80. In other embodiments, the needle 310 is configured to extend above, into or below the blockage, specifically, the needle is configured to not extend deeply into the subdural space.

In order to allow the user to optically see within the evacuation lumen 142 (and/or other components) of the surgical evacuation port device 100, the surgical evacuation port device 100 of the current disclosure includes one or more viewing portions. A viewing portion can be a portion of the surgical evacuation port device that is optically transparent (e.g., evacuation lumen, port body, needle access lumens, bone engagement region, etc.). In some embodiments, the viewing portion may be an optically transparent window provided in one or more components (e.g., evacuation lumen, port body, needle access lumens, bone engagement region, etc.) of the surgical evacuation port device. In some embodiments, other portions of the subdural evacuation port apart from the viewing portion are less transparent compared to the viewing portion, non-transparent or opaque.

Optionally, the surgical evacuation port device 100 may be substantially all optically transparent (e.g., the entire surgical evacuation port device is a viewing portion). In other embodiments, only a portion of the surgical evacuation port device 100, such as the window discussed above or portion of the port body, can be a viewing portion to allow the user to see within the device and detect a blockage and/or determine its location or passage within the evacuation lumen.

As used herein, optically transparent means that light is allowed to pass through the optical transparent material with minimal absorption. In some alternative embodiments, the optically transparent material has a high transparency meaning it allows at least a threshold percentage of light to pass through (e.g., greater than 90%, greater than 95%, or any other suitable percentage) such that it is essentially optically see-through. In some alternative embodiments, the optically transparent material has a medium or medium low transparency or any other suitable transparency allowing at least a threshold of light to pass through (e.g., about greater than 60%, greater than 75%, or any other suitable percentage) that is enough to allow the user to detect a blockage and determine the cause of a blockage, its properties (e.g., size, shape, density, etc.), and/or its location.

For example, a user may visually or optically observe the interior of the evacuation lumen to detect that a blockage has occurred via the viewing portion. Furthermore, the user may view the blockage via the viewing portion to determine the cause of the blockage as being a clot, its properties (e.g., size, shape, density, etc.), and/or its location. The user may use the information to determine an appropriate corrective action for removal of the blockage (for example, by injection of a thrombolytic agent, by breakage, by repositioning, and/or by suction).

In some examples, the entire surgical evacuation port device 100 is formed from an optically transparent material.

In some examples, certain components or portions of the surgical evacuation port device are entirely formed from an optically transparent material. In other words, the viewing portion surrounds such components of the surgical evacuation port device. For example, the port body 140 of the surgical evacuation port device 100 can be optically transparent such that the viewing portion surrounds the evacuation lumen within the port body allowing a user to see within the interior of the evacuation lumen 142. This may allow a surgeon or user to see within the evacuation lumen 142 and optically detect a blockage 80 within the evacuation lumen. In some other examples, only a portion of the port body that defines the evacuation lumen (and/or the evacuation lumen itself) are the viewing portion and are made from an optically transparent material that allows a user to optically see into the evacuation lumen to view obstructions. Typically, the viewing portion of the port body 142 that would be transparent would be a location where blockages commonly form such as near the distal end of the evacuation lumen.

In some embodiments, the bone engagement portion 146 of the port body is optically transparent and forms the viewing portion.

In some other examples, the viewing portion may be a window formed from an optically transparent material located on the device 100. For example, a window may be formed on the port body to allow the user to see within the evacuation lumen of the device and determine whether a blockage has occurred. Typically, the window may be formed on the port body at a location where blockages commonly form such as near the distal end of the evacuation lumen.

Optionally, the user may optically visualize the blockage without the use of non-optical imaging technologies (optical imaging technologies such as a microscope may be used). Optionally, the user may also optically visualize the blockage (and/or pieces or debris thereof) if it is suctioned out via the evacuation lumen before, during, and/or after performance of the operation for blockage removal.

In addition to the viewing portions or windows discussed above for detection of the blockage and/or determining its location and properties, viewing portions may be provided and/or configured such that a user can determine the location and/or monitor the progress of the tool (e.g., a needle or its tip) within the needle access port lumens and/or the evacuation lumen during an operation for removal of a blockage. The rest of the device may be less transparent or opaque.

For example, as depicted in FIGS. 1 and 2, at least a portion of the port body 140 that surrounds the needle access ports 112A, 112B along with certain portions of the needle access ports 112A, 112B may be optically transparent. The transparency can allow a surgeon to optically visualize and monitor an opaque or semitransparent needle that is inserted into the needle access port, determine its location at any time, and/or assess effectiveness of the operation performed by the needle.

In some alternative embodiments, the viewing portion can be a window made of optically transparent material that is located on the device 100 (e.g., glass, a transparent polymer, or any other suitable transparent material) such that a user can see within the access port lumen and determine the location of the tool or needle.

In various embodiment, only the viewing portion of the surgical evacuation port device 100, such as the window or portion of the port body, can be optically transparent to allow the user to see within the device and detect a blockage and determine the location of the needle relative to the blockage while the rest of the device is less transparent or opaque.

In some embodiments, the needle access ports 112A, 112B, the access lumens 116, and the evacuation lumen 142 all include (or are surrounded by) one or more strategically located viewing portions or windows (and/or are fully transparent) to allow the user to see within the evacuation lumen/access lumens and monitor a needle as it extends through the access lumen and into the evacuation lumen while the rest of the device 100 is opaque or less transparent.

It will be appreciated that the entire device 100 can additionally be transparent to allow a user to see through the entire device. The needle access ports 112A, 112B, in combination with the rest of the surgical evacuation port device 200 being transparent, may allow the user to detect a blockage; determine the location and properties of the blockage; monitor the location and/or passage of the needle through the ports into the lumen; determine the effectiveness of a thrombolytic agent, if the needle is used to inject a thrombolytic agent; determine the effectiveness of the needle's suctioning of the blockage/debris; and/or determine if the blockage requires further intervention such as injection of more thrombolytic agent, change in location of the needle tip, withdrawal/suction via the needle, or any other suitable change. Optionally, the user may also optically visualize the blockage (and/or pieces or debris thereof) if it is suctioned out via the access port lumen before, during, and/or after performance of the operation for blockage removal.

Figure 3:
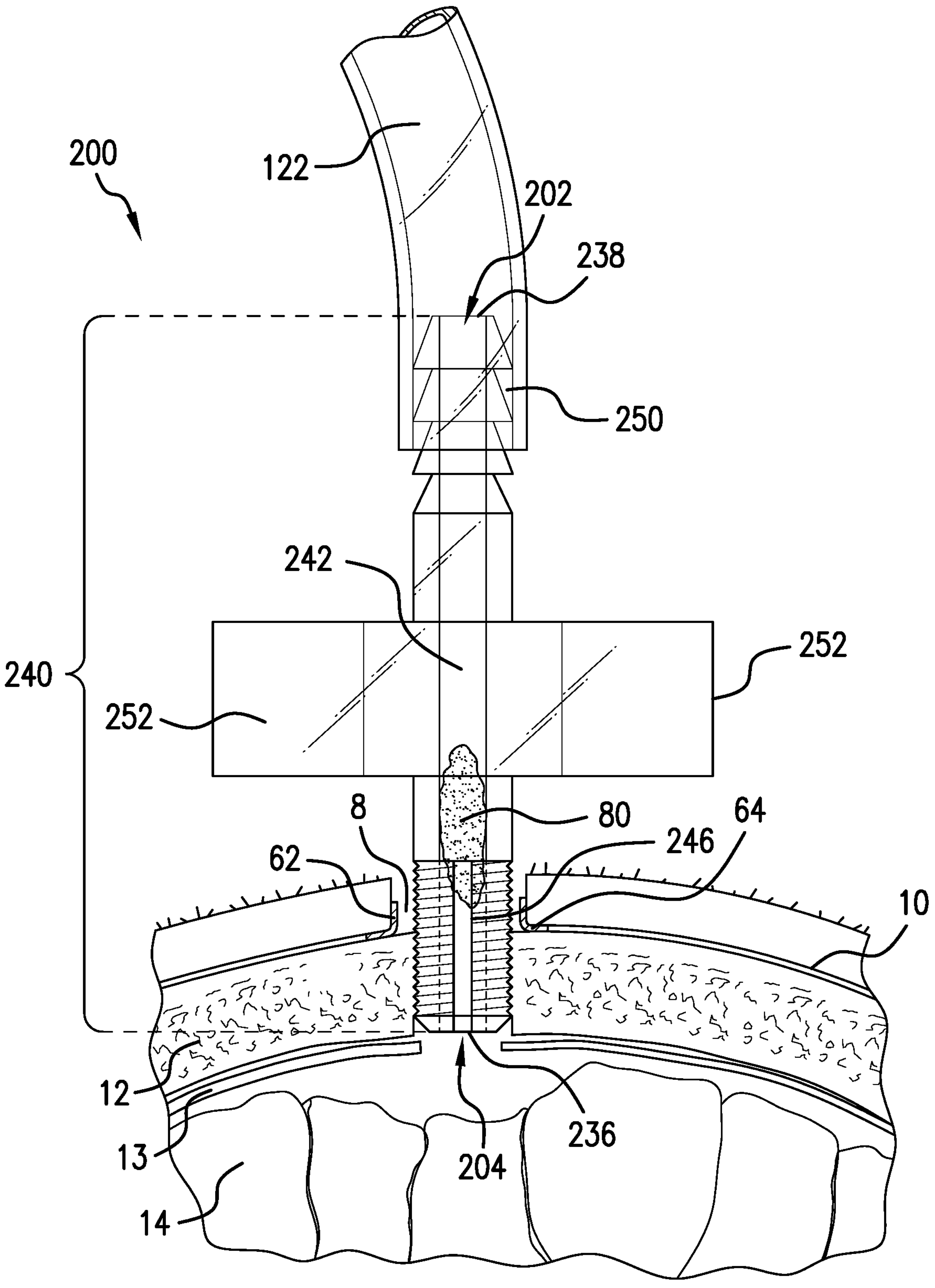
FIG. 3 is a side view of an embodiment of a transparent surgical evacuation port device and mounted within a skull of a patient, in accordance with the present disclosure.
Figure 4:
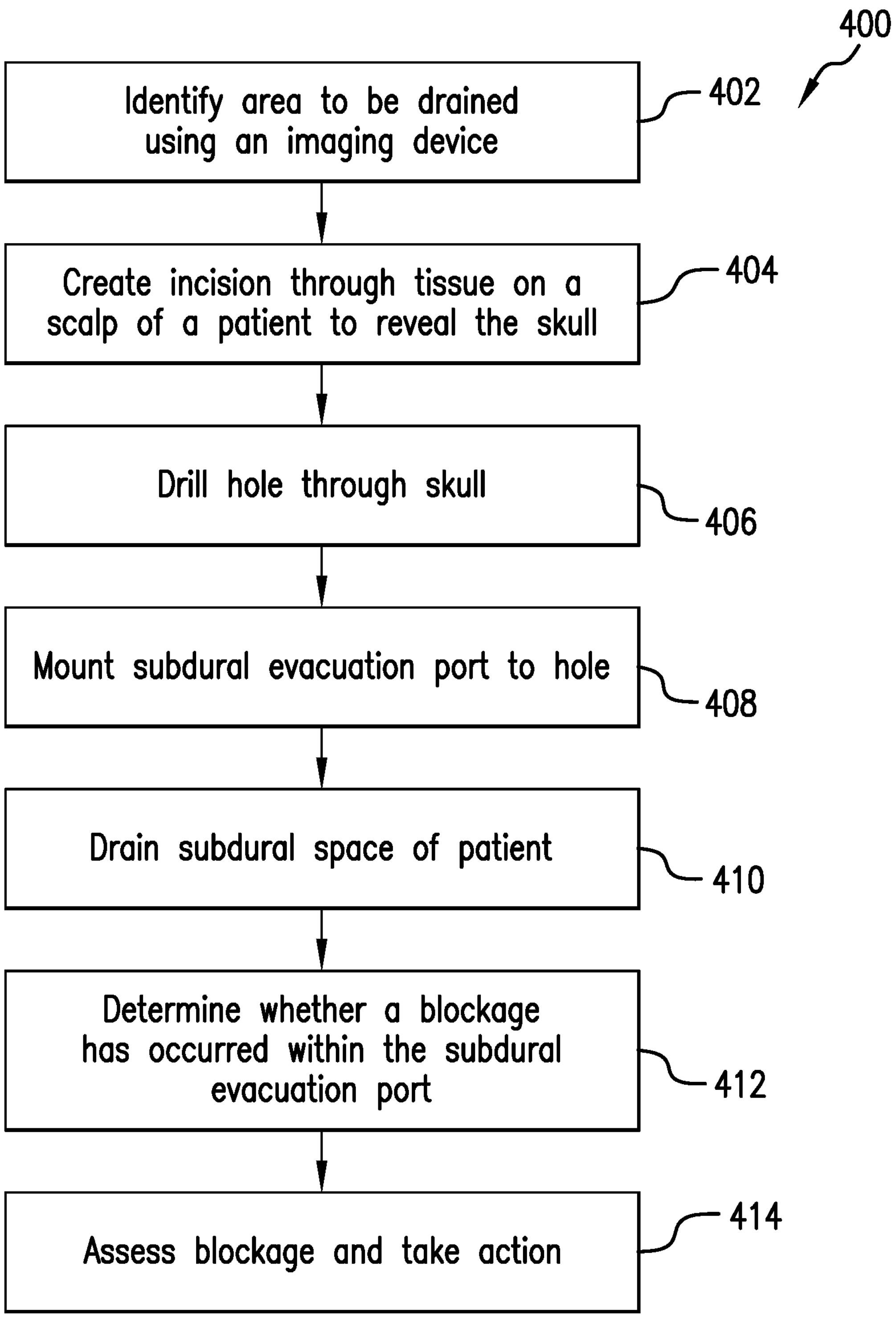
FIG. 4 is a flow-chart illustrating a method of using a transparent surgical evacuation port device, in accordance with the principles of the present disclosure.

Referring now to FIG. 3, as alternate embodiment of the surgical evacuation port device 200 is depicted as mounted within the hole 8. The surgical evacuation port device of FIG. 3 is similar those shown in FIGS. 1 and 2, albeit it does not include the needle access ports. The surgical evacuation port device 200 includes a port body 240 extending between a distal and proximal end 236, 238. The device includes a distal evacuation opening 204 and a proximal evacuation opening 202. The surgical evacuation port device 200 includes a bone engagement region 246 engaged with a skull 12. A retractor having arms 62, 64 is depicted retracting a scalp 10 of a patient. It will be appreciated that in some embodiments a retractor is not used and the incision on the scalp 10 is held open by the device 100 (e.g., see FIGS. 1 and 2). As depicted, fluid can be withdrawn using the device 200 from the subdural space beneath the dura 13 to relieve pressure on the brain 14 through the conduit 122 which can be connected to a suction device similar to the suction device 40 discussed above. The conduit is mounted to a fitting 250.

At least a portion of the port body 240 that defines the evacuation lumen 242 is a viewing portion made from an optically transparent material that allows a user to optically see into the evacuation lumen to view obstructions therein without altering the suction pressure and/or without causing other issues. The viewing portion can be the entire port body that surrounds the evacuation lumen, a window provided in the port body, or the like.

When the blockage 80 is detected via the viewing portion, the user can assess the cause, location, and/or properties of the blockage 80 and take appropriate action, as discussed above. For example, the user can introduce a thrombolytic agent to the blockage site to assist in dissolving the blockage. The user can additionally determine the effectiveness of a thrombolytic agent, stop suction, and remove the conduit and insert a needle through the evacuation lumen and surgical evacuation port device to break up a blockage an/dor determine if the blockage requires further intervention such as withdrawal of the surgical evacuation port device 200 and stopping the procedure. In other embodiments, the user can increase the suction within the evacuation lumen 242 to assist with withdrawal of the blockage.

The subdural evacuation port 200 additionally includes wings 252. The wings are formed at the body 240 between the distal and proximal ends 236, 238. The wings 252 are configured to allow the device 200 to be screwed into a hole within bone, such the hole 8 in the skull 12, by hand. It will be appreciated that any other tightening mechanism can additionally be used. For example, a removeable device, a ratcheting mechanism or any other suitable devices.

In some embodiments, the port body 140, 240, of either of the subdural evacuation ports 100, 200 discussed above, or any other viewing portion or suitable viewing portion of the subdural evacuation ports 100, 200 can be formed from an optically transparent or an optically semi-transparent (as discussed above) material. In some embodiments, the material is a polymer. In some embodiments, examples of the material can include, without limitation, crystalized ABS, polycarbonate, or a transparent ceramic such as aluminum oxynitride, glass, acrylic or any other medical grade, shatter resistant materials. In some embodiments, the surgical evacuation port device can be formed from a material that has a substantially low thrombogenicity, is optically transparent and sufficiently rigid to sustain a vacuum or any combination of properties as discussed above.

As disclosed herein the port body 140, 240 (or other portions of the subdural evacuation ports 100, 200) can be made of suitably rigid materials, stiff plastics, glass, transparent ceramic or any other suitable material. In some embodiments, the surgical evacuation port device is made from a material that is sufficiently rigid to be screwed into a skull of a human. In some examples, the surgical evacuation port device is formed from a material that is sufficiently rigid to not collapse when subjected to suction pressure applied for removal of fluid and or the blockage. In some embodiments, the material is sufficiently stiff polymer.

In some embodiments, the surgical evacuation port device 100, 200 is made from a material having a substantially low thrombogenicity (e.g., thrombogenicity means the tendency to of material in contact with blood to form a thrombus or clot), such that it does not cause blood clotting or minimizes blood clotting. In some embodiments, the material is substantially less thrombogenic than stainless steel. In some examples, the material is half as thrombogenic as stainless steel. In other examples, the material is less than half as thrombogenic as stainless steel. Other suitable embodiments are additionally possible. In some embodiments, the portion that engages with the skull (e.g., the bone engagement portions 146, 246) is formed from a material having a material having a substantially low thrombogenicity.

In a preferred embodiment, the device is formed from a rigid material as discussed above, that has a low thrombogenicity as discussed above and is optically transparent. Although any other combination of the material properties discussed above is additionally possible.

Referring to FIG. 3, a flow chart illustrating an example method for draining the subdural space of a patient using, for example, the surgical evacuation port devices 100, 200. Prior to the steps provided by the flowchart, anesthesia such as local or general anesthesia can be given to the patient. The flowchart includes a step 402 of identifying a location desired to be drained on a patient. In some examples, the location is identified using imaging technology (e.g., CT, X-ray, or MRI). In some embodiments, the location is an area on the patient with the greatest subdural hematoma thickness. A step 404 includes creating an incision on the scalp of a patient. In some embodiments, the incision can be made through skin, subcutaneous tissue, galea, and periosteum. In a step 406 a hole is drilled at the location of the incision. The hole can be drilled using a suitable surgical drill as discussed above. In some examples, the drill is adjusted based on the imaging provided by step 402 such that the drill does not drill beyond the desired depth allowing the drill to advance until the drill reaches the space that is desired to be drained and can be withdrawn removing any bone fragments from the skull. Optionally, a retractor can then be provided at the incision (such as depicted in FIG. 1, FIG. 2 depicts an example without the use of a retractor). At a step 408 a surgical evacuation port device such as the surgical evacuation port devices 100, 200 is mounted and secured into the hole. The surgical evacuation port devices 100, 200 are mountable using threads at their skull engagement regions. It will be appreciated that any other suitable skull engagement region, as discussed above, is additionally possible. In a step 410, the subdural space of the patient can be drained using the methods provided herein, this step additionally includes piercing the dura of a patient to allow access to the subdural region. At a step 412 it is determined whether a blockage has occurred within the surgical evacuation port device. This can be determined by a user by optically visualizing one or more portions of the surgical evacuation port device (e.g., via a viewing portion, via a window, and/or when the whole device is transparent).

If a blockage occurs at the drainage location, step 414 provides optically viewing and assessing the location and/or properties of the blockage and determining an appropriate action for removal of the blockage. In some examples, the blockage is removed using a tool through a needle access port of a surgical evacuation port device such as the surgical evacuation port device 200 and the needle 218 as discussed herein. The user can optically view the blockage, as discussed herein, and select a needle having an appropriate length to extend into, below, or before the blockage. In some examples, the user can introduce a thrombolytic agent, as discussed above, to assist with dissolving the blood clot. In other examples, the user can withdraw the blockage (and/or pieces or debris thereof) via a tool such as the needle. Given the optically transparency aspects described in this disclosure, the user can determine the effectiveness of the operation being performed and adjust the removal step accordingly. For example, the user can optically determine the effectiveness of the thrombolytic agent by looking through the device. The user can additionally suction or aspirate the blockage (or debris/pieces thereof) if it is determined that the thrombolytic agent is unable to completely dissolve the blockage. The blockage (or debris/pieces thereof) may be aspirated or suctioned by a user by positioning the needle at the correct location for aspiration while looking through the device given the optically transparency in accordance with this disclosure.

In some other embodiments, the blockage (or debris/pieces thereof) may be aspirated or suctioned by adjusting the amount of suction pressure within the evacuation lumen to suction or aspirate the blockage via the evacuation lumen. A user may monitor the progress of the blockage through the evacuation lumen via a viewing portion, window or transparent portion thereof.

It will be appreciated the steps outlined above include other steps discussed throughout the present disclosure and are for explanatory purposes, for example penetrating the dura of the patient prior to draining the hole. Once, the drainage is complete, the device can be left within the skull and imaging technology can be used to determine to determine if the fluid has been completely evacuated from the subdural layer of the brain. The device can be removed once evacuation has completed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A surgical evacuation port device, comprising:

a port body including:

a distal end defining a distal evacuation opening, a proximal end defining a proximal evacuation opening, an evacuation lumen defined within the port body and extending from the distal evacuation opening to the proximal evacuation opening, and a viewing portion of the port body that is made from an optically transparent material that allows a user to optically see through the viewing portion and into the evacuation lumen to view obstructions therein; and a bone engagement portion associated with the port body and configured to attach to a bone to enable evacuation of fluid through the evacuation lumen.

2. The surgical evacuation port device of claim 1, wherein the viewing portion is a window, and a remainder of the port body around the window is less transparent or opaque.

3. The surgical evacuation port device of claim 1, wherein the viewing portion surrounds the evacuation lumen.

4. The surgical evacuation port device of claim 1, wherein the entire port body is formed from the optically transparent material.

5. The surgical evacuation port device of claim 1, wherein the proximal end includes a fitting configured to operably connect to a suction device.

6. The surgical evacuation port device of claim 1, wherein the bone engagement portion is configured to mount the port body through a hole in the bone to evacuate fluid through the evacuation lumen across the bone.

7. The surgical evacuation port device of claim 1, wherein the bone engagement portion includes threads disposed about the exterior of the distal end of the port body and configured to screw into bone.

8. The surgical evacuation port device of claim 7, wherein the threads are configured and dimensioned to screw into a skull to position the port body in communication with a subdural region of a cranium.

9. The surgical evacuation port device of claim 1, wherein at least a portion of the bone engagement portion is optically transparent to allow the user to optically see into the evacuation lumen.

10. The surgical evacuation port device of claim 1, further comprising:

a needle access port defining an access port lumen in communication with the evacuation lumen to perform an operation at a site of a blockage therein; and a seal that seals the needle access port to preserve a suction within the evacuation lumen.

11. The surgical evacuation port device of claim 10, wherein the needle access port includes an access port viewing portion formed from an optically transparent material to allow the user to see therein.

12. The surgical evacuation port device of claim 1, wherein the viewing portion is made from an optically transparent polymer.

13. The surgical evacuation port device of claim 12, wherein the optically transparent polymer is polycarbonate.

14. The surgical evacuation port device of claim 12, wherein the optically transparent polymer is crystalized acrylonitrile butadiene styrene (ABS).

15. The surgical evacuation port device of claim 1, wherein the optically transparent material is sufficiently rigid to withstand suction within the evacuation lumen without collapsing.

16. A surgical evacuation port device comprising:

a port body including:

a distal end defining a distal evacuation opening, a proximal end defining a proximal evacuation opening, an evacuation lumen defined within the port body and extending from the distal evacuation opening to the proximal evacuation opening, and a viewing portion of the port body that men is made from an optically transparent material that allows a user to optically see through the viewing portion and into the evacuation lumen to view obstructions therein; and a bone engagement portion associated with the port body and including threads that are configured and dimensioned to screw into a skull to position the port body in communication with a subdural region of a cranium; and a fitting associated with the port body configured to attach to a suction device to provide suction to the subdural region of the cranium.

17. The surgical evacuation port device of claim 16, wherein the viewing portion is a window and a remainder of the port body is less transparent or opaque.

18. The surgical evacuation port device of claim 16, wherein the viewing portion surrounds evacuation lumen.

19. The surgical evacuation port device of claim 16, wherein the entire port body is formed from the optically transparent material.

20. The surgical evacuation port device of claim 16, further comprising:

a needle access port defining an access port lumen in communication with the evacuation lumen to perform an operation at a site of a blockage therein, and a seal that seals the needle access port to preserve suction within the evacuation lumen.

21. The surgical evacuation port device of claim 20, wherein the needle access port includes an access port viewing portion formed from an optically transparent material to allow the user to see therein.

22. The surgical evacuation port device of claim 16, wherein the optically transparent material is sufficiently rigid to withstand the suction within the evacuation lumen without collapsing.

* * * * *